United States Patent [19]
Bolton

[11] Patent Number: 5,906,632
[45] Date of Patent: May 25, 1999

[54] INTRATUNNEL ATTACHMENT DEVICE AND SYSTEM FOR A FLEXIBLE LOAD-BEARING STRUCTURE AND METHOD OF USE

[75] Inventor: Carl William Bolton, Santa Barbara, Calif.

[73] Assignee: Innovasive Devices, Inc., Marlborough, Mass.

[21] Appl. No.: 08/943,457

[22] Filed: Oct. 3, 1997

[51] Int. Cl.⁶ .................................................. A61B 17/04
[52] U.S. Cl. .............................................................. 606/232
[58] Field of Search ............................. 606/232; 411/457

[56] References Cited

U.S. PATENT DOCUMENTS

| | | | |
|---|---|---|---|
| 5,423,860 | 6/1995 | Lizardi et al. | 606/232 |
| 5,667,513 | 9/1997 | Torrie et al. | 606/104 |
| 5,707,395 | 1/1998 | Li | 606/232 |

*Primary Examiner*—Gary Jackson
*Attorney, Agent, or Firm*—Allen, Dyer, Doppelt, Milbrath & Gilchrist, P.A.

[57] ABSTRACT

A device for urging a flexible member against an inner surface of a bone tunnel includes a deformable ring that has a bore extending from a first side to a second side and a proximal cutout at a proximal end that extends from an outer surface into the bore. The ring is dimensioned to slide within a bone tunnel and is adapted to permit a positioning of a pair of end segments of a flexible member between two opposed generally flat sections of the ring and an inner wall of the bone tunnel. In position the flat sections are generally parallel to a tunnel longitudinal axis. The ring is expandable from a collapsed state wherein the first and the second sections are a first distance apart to an expanded state wherein the first and the second sections are a second distance apart greater than the first distance. The device further includes a screw that is insertable through the proximal cutout into the ring bore for expanding the flat sections outward. Such an expansion is for urging the ring's outer surface against the flexible member end segments to retain the flexible member end segments against the bone tunnel's inner wall.

35 Claims, 8 Drawing Sheets

INTRATUNNEL ATTACHMENT DEVICE AND SYSTEM FOR A FLEXIBLE LOAD-BEARING STRUCTURE AND METHOD OF USE

BACKGROUND OF THE INVENTION

1. Field of the Invention

The present invention relates to orthopedic devices and methods for attaching flexible members to a bone, and, more particularly, to such devices and methods for attaching flexible load-bearing members within a tunnel of a bone.

2. Description of Related Art

Orthopedic surgical procedures sometimes require an attachment (or reattachment) of a flexible member to a bone. The flexible member might comprise soft tissue such as a ligament or tendon, a synthetic element, or suture. Devices and methods are known in the art to accomplish such an attachment, including those for affixing the flexible member within a hole of the bone.

For example, it is known to use a member such as a screw to press at least one end of the flexible member against the interior wall of a bone space (Mahony, U.S. Pat. No. 5,062,843; Roger et al., U.S. Pat. No. 5,383,878; Steininger et al., U.S. Pat. No. 5,425,767; Huebner, U.S. Pat. No. 5,454,811; Laboureau, EU 0 317 406). It is also known to anchor a ligament between two elements, the inner one deformable (U.S. Pat. No. 5,108,431), and to pass a ligament through a center of a device, creating tension by relative movement of elements (DeSatnick, U.S. Pat. No. 5,571,184).

A particular surgery in which flexible member attachment is required is endosteal fixation, wherein the terminal ends with bone plugs of an anterior cruciate ligament graft replacement material are attached within bone tunnels. The attachment is often achieved by compressive or interference fit means.

However, there is no known effective method for securely affixing two free ends of an entirely soft tissue graft (i.e., without bone plugs attached) so that the entire fixation element is confined within the bounds of the bone tunnel.

SUMMARY OF THE INVENTION

It is therefore an object of the present invention to provide a device and method for affixing a flexible member to a bone.

It is an additional object to provide such a device and method for affixing a flexible member end segment within the confines of a bone tunnel.

It is a further object to provide such a device and method that does not compromise the mechanical integrity of the flexible member.

It is another object to provide such a device and method that does not interfere with the healing of the flexible member.

It is yet an additional object to provide such a device and method that does not employ bone plugs in the attachment.

It is yet a further object to provide a system for inserting the fixation device into a bone tunnel.

It is yet another object to provide a probe for measuring a void space in the bone tunnel prior to the device insertion.

It is an additional object to provide a device that is easily removable from the bone tunnel if desired.

It is a further object to provide a device that is insertable while the flexible member is under tension.

These objects and others are attained by the present invention, a device and method for affixing a flexible member within a bone tunnel. The device comprises an expandable member that has a first section, a second section in mechanical connection with the first section, and a space therebetween. An opening extends from outside the expandable member into the space. The expandable member is dimensioned to slide within a bone tunnel and is adapted to permit a positioning of the flexible member end segment between the first section and an inner wall of the bone tunnel. The expandable member is expandable from a collapsed state wherein the first and the second sections are a first distance apart to an expanded state wherein the first and the second sections are a second distance apart greater than the first distance.

The device also comprises means insertable through the proximal opening into the space for expanding the expandable member from the collapsed state to the expanded state sufficiently far to urge the expandable member first section against the flexible member end segment. This expansion serves to press and retain the flexible member end segment against the bone tunnel inner wall.

In a particular embodiment, the expanding member comprises a deformable ring having a bore extending from a first side to a second side and a proximal cutout at a proximal end extending from an outer surface into the bore.

In a preferred embodiment the expanding means comprises a tapered member that is insertable through the proximal cutout into the ring bore. The tapered member has a smaller distal end tapering to a larger proximal end, so that an insertion of the distal end into the ring bore via the proximal cutout causes a progressive expansion of the ring.

Thus it can be seen that an expansion of the device transfers a radial expanding force to the flexible member end segment, preferably without disrupting the physical integrity thereof. In addition, the fixation is accomplished without the use of bone plugs.

The method of the present invention comprises the steps of positioning a flexible member end segment, preferably two flexible member end segments, into a bone tunnel. Next an expanding member in the collapsed state is inserted into the bone tunnel, so that the flexible member is positioned between an inner wall of the bone tunnel and an outer surface of the expanding member. Then the expanding member is expanded, so as to urge the outer surface thereof against the flexible member. This urging serves to compress the flexible member(s) against the inner surface of the bone tunnel and to retain the flexible member(s) in place. This may be accomplished while tension is applied to the flexible member(s).

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–6G.

Figure 4:
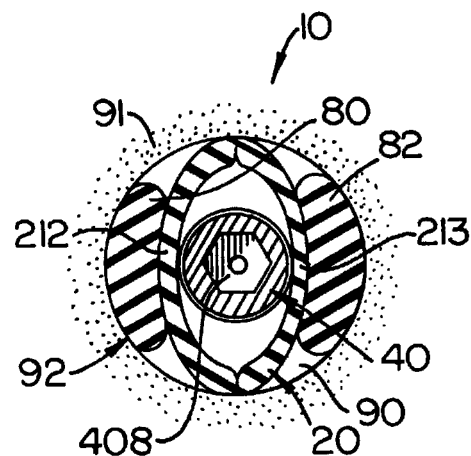
FIG. 4 is a proximal end cross-sectional view of the device in place, normal to the bone tunnel, anchoring two ends of a flexible member within a bone tunnel.
Figure 5:
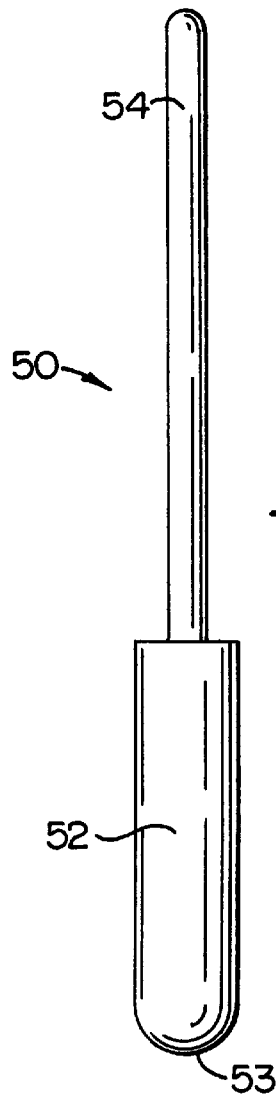
FIG. 5 is probe useful for gauging the space within a bone tunnel.
Figure 6B:
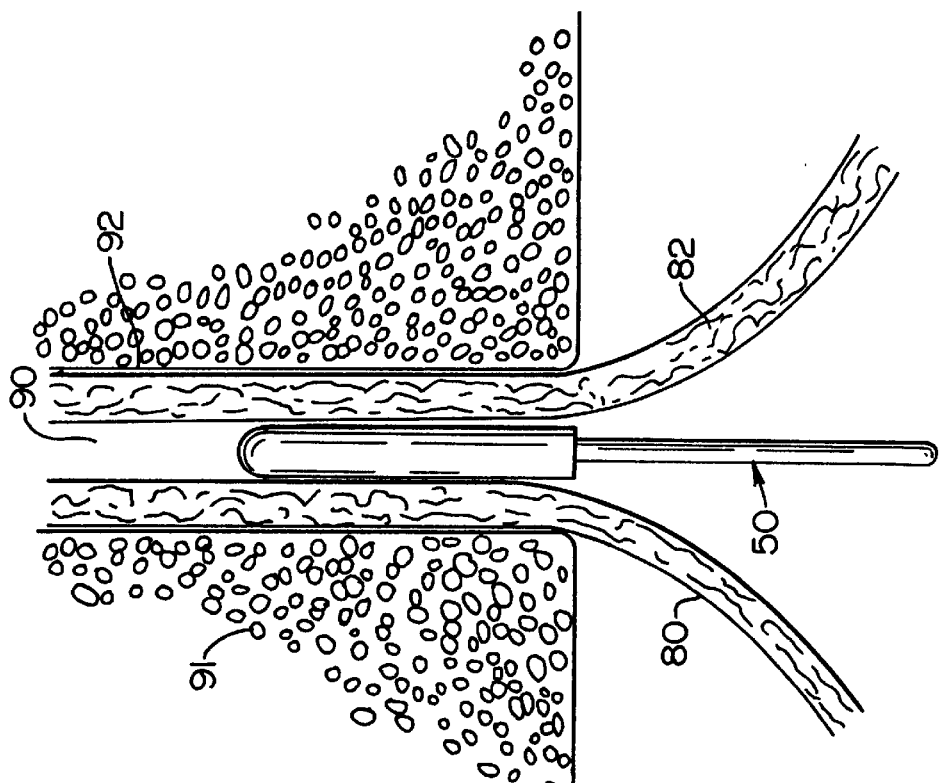
FIG. 6 illustrates the steps from a cross-sectional view of the method of the present invention, including (A) positioning the flexible member ends into a bone tunnel; (B) measuring the void space remaining in the tunnel with a probe to assist in choosing a proper-diameter cannulated screw; (C) positioning an inserter loaded with a deformable ring with a guide pin and repositioning suture at the opening of the bone tunnel containing a pair of flexible members; (D) positioning the deformable ring with the guide pin and retention suture into the bone tunnel between the flexible members; (E) inserting the screw into the ring bore along the guide pin; (F) deforming the ring into an expanded state, urging the flexible members against the bone tunnel inner wall; and (G) removing the screw from the ring with a driver to enable removing the ring from the tunnel.
Figure 6A:
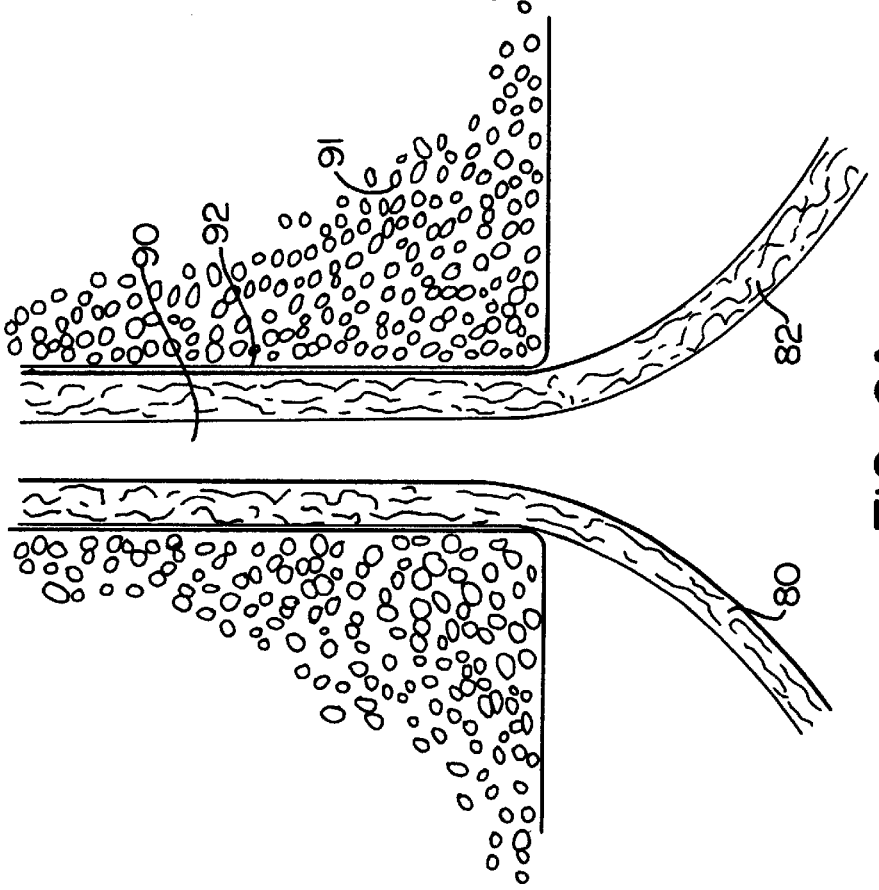
Figure 6C:
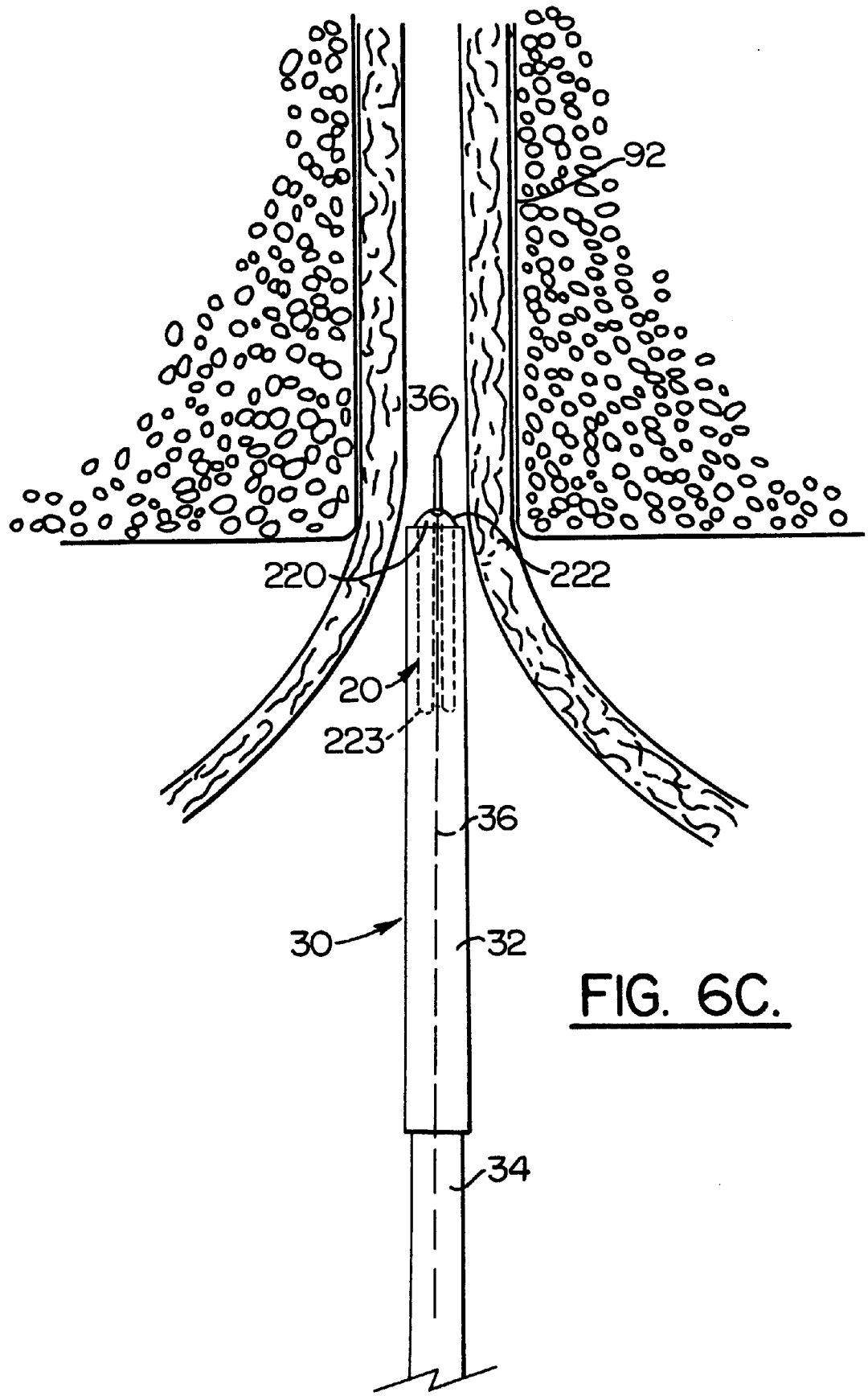
Figure 6D:
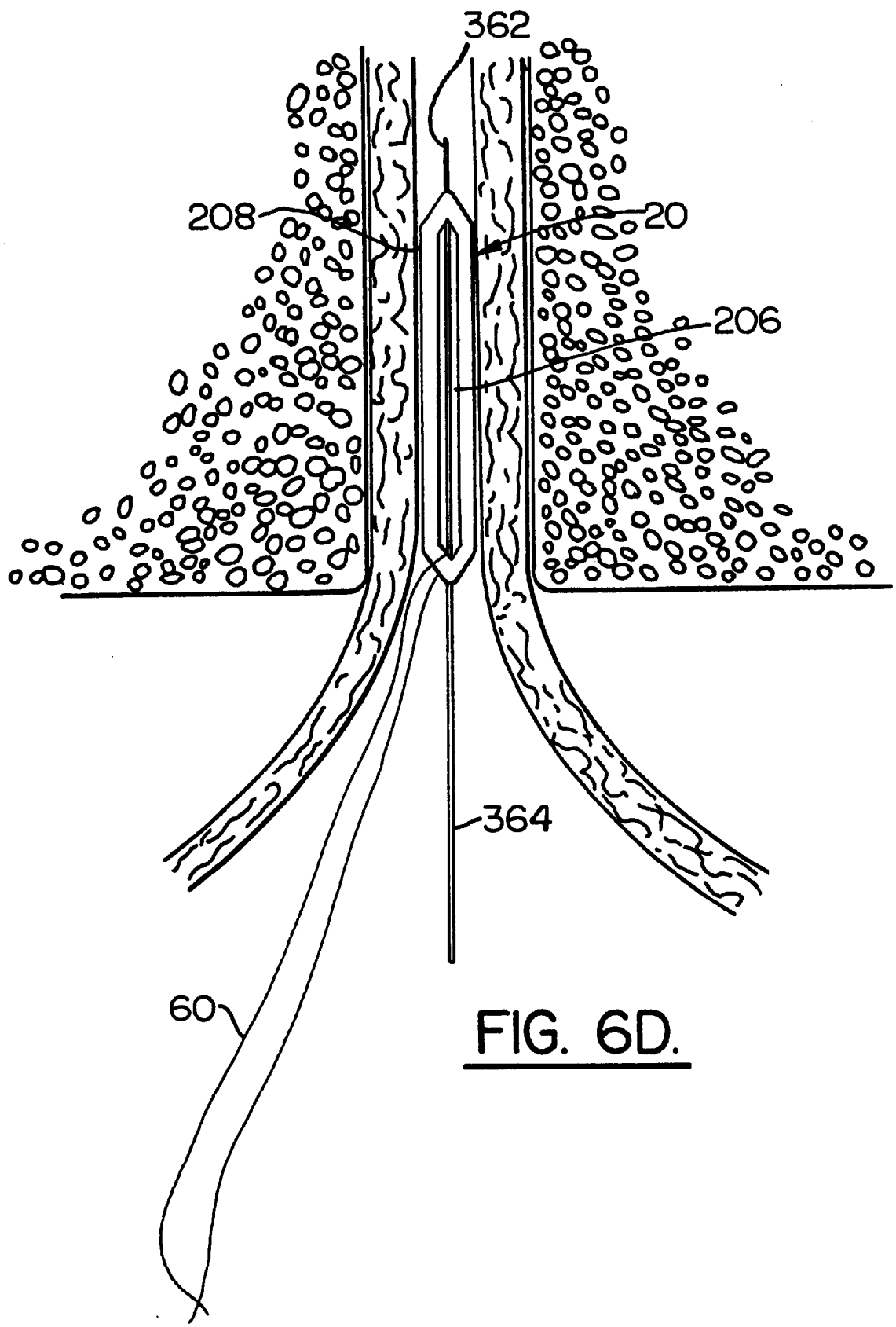
Figure 6E:
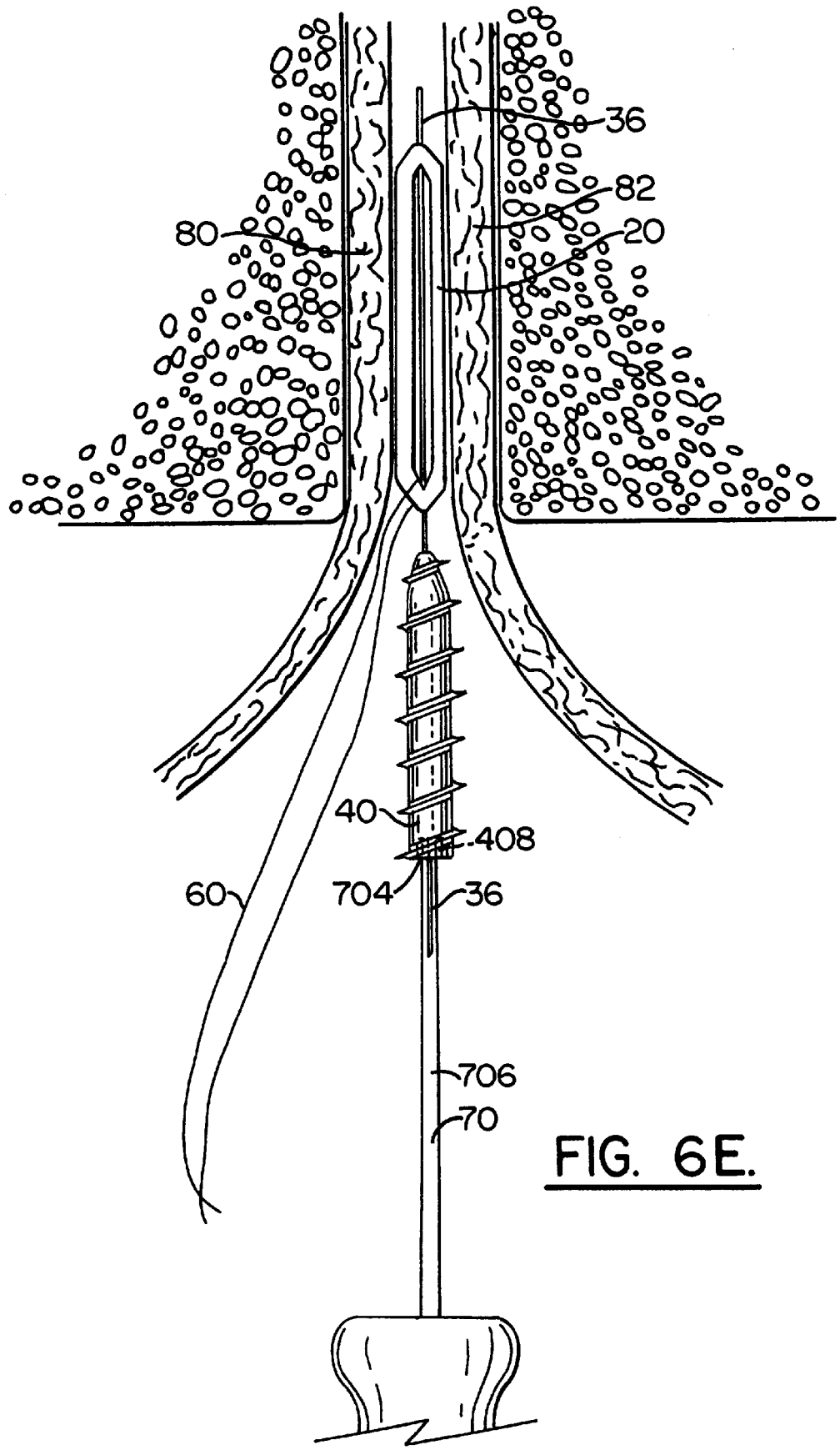
Figure 6F:
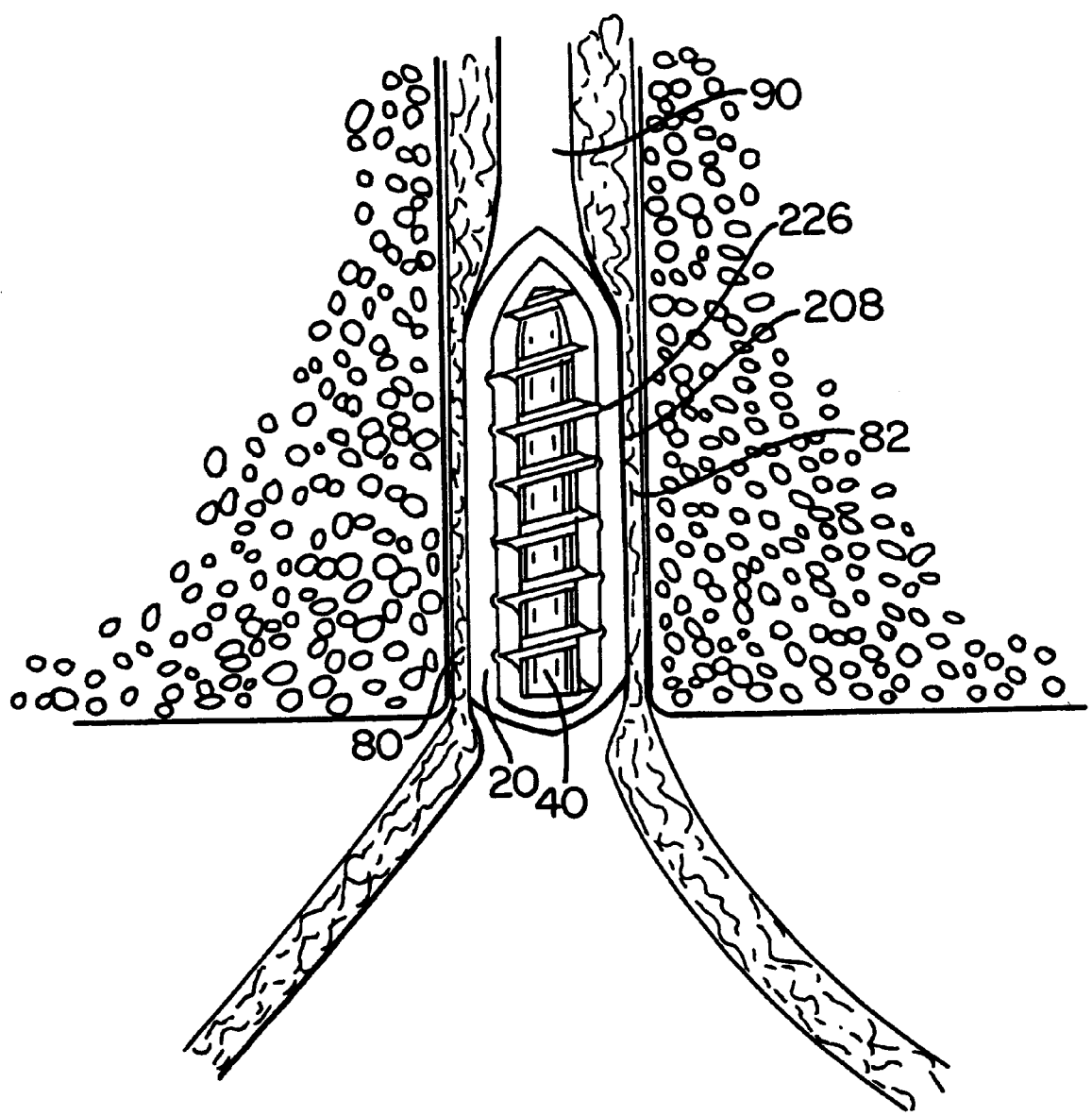

The device 10 is for affixing a flexible member, and preferably two end segments, hereafter referred to as "ends," of a flexible member 80,82, within a bone tunnel 90 in a bone 91 (see FIGS. 4 and 6F). Such a flexible member may comprise soft tissue or a synthetic element and is preferably a load-bearing structure such as a natural or artificial ligament or tendon, including, but not limited to, a semitendinosus tendon, a gracilis tendon, an iliotibial band, or allograft.

The device 10 comprises a deformable ring 20 (FIG. 1) that has a bore 206 extending from a first side 202 to a second side 204. The ring 20 is dimensioned, when in a collapsed state, to slide within the bone tunnel 90 so that the sides 202,204 are generally parallel to the bone tunnel 90.

In a preferred embodiment the ring 20 in a free state has a generally elliptical shape in a cross section generally normal to the bore 206, although this is not intended as a limitation. The ring 20 has two opposed, flatter sections 212,213 along the major longitudinal axis thereof joined by generally U-shaped sections 214,215, one at the distal end 222 and one at the proximal end 223.

These U-shaped sections 214,215 may further be described as "living hinges," as the ring's deformation is accomplished owing to the malleability of these portions of the ring 20. This shape is adapted to permit the flexible member ends 80,82 to fit between the bone tunnel's inner wall 92 and the flatter sections 212,213 (see FIGS. 4 and 6D) when in the collapsed state. The deformable ring 20 further has a pair of cutouts 220,221 therethrough that extend from the ring's outer surface 208 to the inner surface 216. The cutouts 220,221 are positioned one in each U-shaped section 214,215, such that the cutout 220 at the distal end 222 has a diameter sufficient to accommodate a guide pin 36, and the cutout 221 at the proximal end 223 has a diameter sufficient to accommodate a cannulated screw 40. The ring 20 further has a pair of opposed grooves 218 extending from the distal cutout 220 to the proximal cutout 221. These grooves 218, when the ring 20 is in the collapsed state, wherein the flat sections 212,213 are adjacent, form a tunnel sufficiently large to accommodate a guide pin 36 inserted thereinto (see FIGS. 3A, 3B, and 6D). In use, as will be described more fully below, the guide pin 36 is for guiding the insertion of a cannulated screw 40 into the ring 20.

The ring 20 further has means for facilitating a gripping of the flexible members 80,82 thereagainst. In a preferred embodiment the gripping means comprises a plurality of generally transversely extending grooves 210 in the ring's outer surface 208 along the flatter sides 212,213. This particular gripping means is not intended as a limitation, as one of skill in the art could anticipate other embodiments, such as protrusions or barbs adapted to engage the flexible members.

The ring's flat sections 212,213 additionally have a width 224 that is adapted for insertion into the chosen bone tunnel 90. It is anticipated that a plurality of rings 20 would be available, from which the user may choose depending upon the bone tunnel 90 to be utilized.

In a preferred embodiment the ring 20 comprises a compliant material, such as a polymer like polyethylene, for example, high-molecular-weight polyethylene. The material may also comprise a bioabsorbable polymer. These suggested materials are not intended as limitations, as additional materials may be conceived by one of skill in the art.

Figure 1:
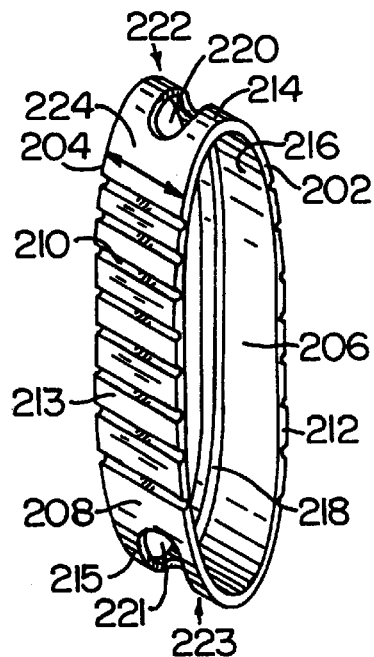
FIG. 1 is a side perspective view of the deformable ring of the present invention.
Figure 2:
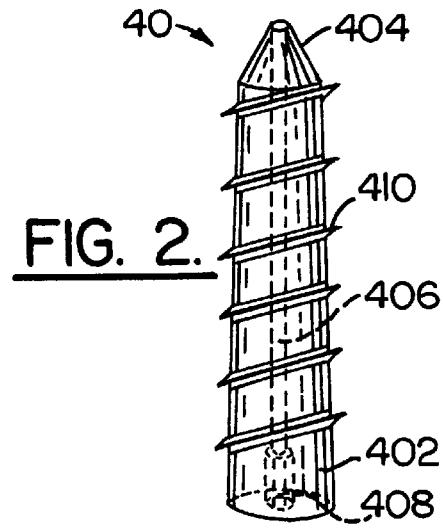
FIG. 2 is a side perspective view of the cannulated screw of the present invention.

The device 10 also comprises means insertable within the ring bore 206 for expanding a portion of the ring 20 outward. This motion is for deforming the ring 20 as described above. In a preferred embodiment the expanding means comprises a tapered member, preferably a screw member, in a most preferred embodiment a cannulated screw 40, that has a bore 406 extending from the distal end 404 to the proximal end 402, the bore 406 dimensioned to permit the guide pin 36 to pass therethrough. The screw 40 further has threads 410 adapted to achieve purchase of the ring's inner surface 216 (FIG. 2). Preferably the ring 20 material has sufficient malleability that the insertion of the screw 40 will form a helical groove 226 (FIG. 6F) in the ring's inner surface 216, helping to retain the screw 40 in place within the ring 20. The screw 40 may, for example, be made of metal, or of a bioabsorbable material, although these are not intended as limitations.

The screw 40 has a smaller distal end 404 that tapers to a larger proximal end 402, so that an insertion of the distal end 404 into the ring's bore 206 causes a progressive expansion of the ring 20. This insertion is accomplished by placing the screw's distal end 404 into the ring's proximal cutout 221 and rotating the screw 40 until the screw 40 is encompassed within the ring's bore 206 (FIG. 6F). Preferably the distal cutout 220 is dimensioned to prevent the screw 40 from passing therethrough. Thus the cannulated screw 40 facilitates a deformation of the ring 20 from a collapsed position wherein the flatter sides 212,213 are a first distance apart (FIG. 6D) and an expanded position wherein the flatter sections 212,213 are bowed outward about the U-shaped sections 214,215 and are a second distance apart greater than the first distance (FIG. 6F). In this position the flexible member ends 80,82 are urged and retained against the tunnel's inner wall 92.

In a preferred embodiment, the free state (FIG. 1), wherein the ring 20 is under no tension, comprises a position between the collapsed position (FIG. 6D) and the expanded position (FIG. 6F).

The screw 40 also has driving means at the proximal end 402 for aiding in the insertion of the screw 40 into the ring's bore 206. In a particular embodiment the driving means comprises a hole shaped to receive a driver, for example, a hex-shaped hole 408 for driving by a hex driver 70.

This driving means is not intended as a limitation, however, as alternate means of providing drivability may be contemplated by one of skill in the art, such as a protrusion adapted to engage a depression in a driving tool. In the particular embodiment shown, the hex driver 70 additionally has an axial bore 706 extending from a distal end 704. The axial bore 706 extends into the driver 70 sufficiently far to encompass the portion of the guide pin 36 that extends proximal of the ring's proximal cutout 221 (FIG. 6E).

Figure 3A:
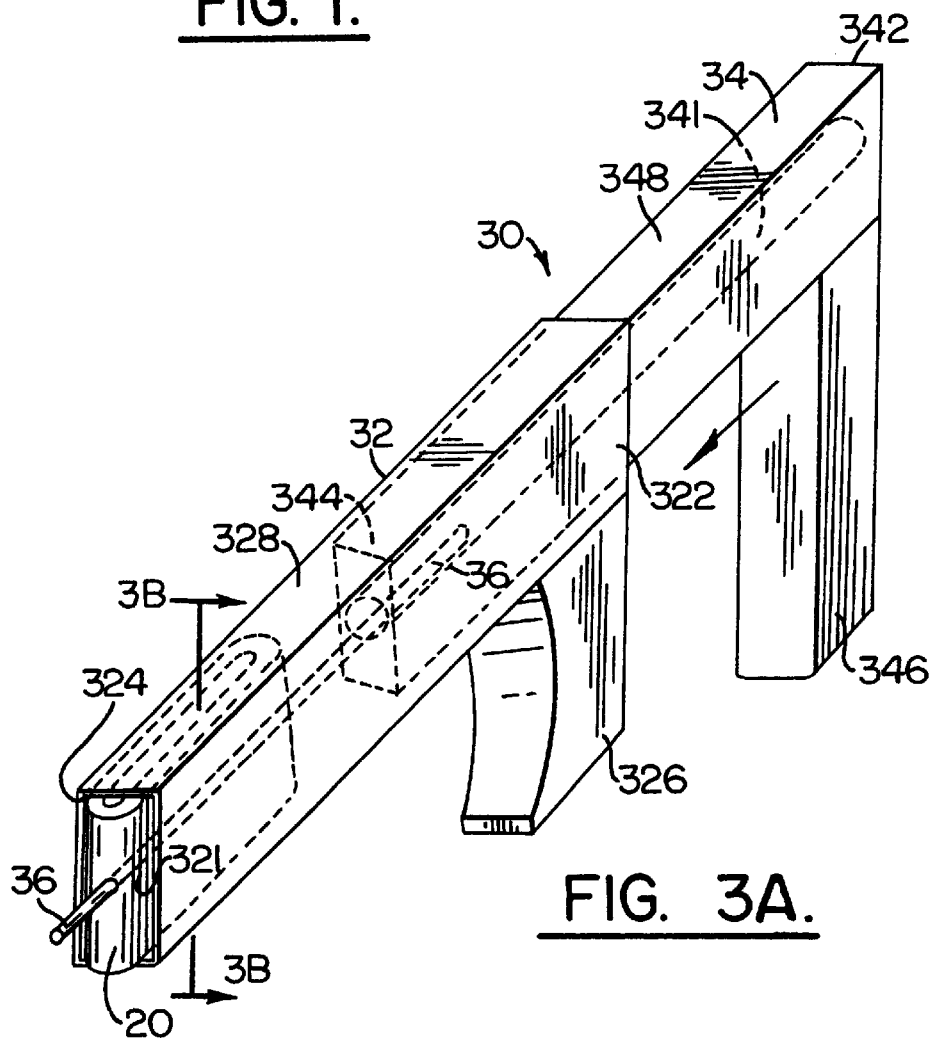
FIG. 3A is a perspective exploded view of the inserter sleeve-stylet combination, loaded with a deformable ring and guide pin.
Figure 3B:
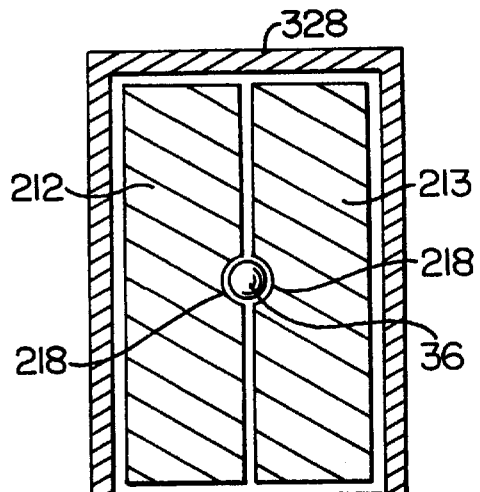
FIG. 3B is a cross-sectional view along line 3B—3B in FIG. 3A showing the inserter sleeve, deformable ring, and guide pin.

An inserter 30 for inserting the ring 20 into a bone tunnel 90 is also provided within the scope of the present invention. As shown in FIG. 3A, a particular embodiment of the inserter 30 comprises an inserter sleeve 32, which has a downwardly extending handle portion 326 affixed at a proximal end 322. A longitudinally extending hollow portion 328 has a bore 321 therethrough from the proximal end 322 to the distal end 324. The bore 321 is dimensioned to permit the admittance of a deformed ring 20 in the collapsed state at the proximal end 322 and its advancement through the bore 321 to the distal end 324..

The inserter 30 further comprises an inserter stylet 34, which also has a downwardly extending handle portion 346 at a proximal end 342. A longitudinally extending hollow plunger 348 has a bore 341 therethrough from the proximal end 342 to the distal end 344. The plunger 348 has an outer dimension adapted for insertion into the sleeve bore 321 from the sleeve's proximal end 322, the insertion stopped by the handle portion 346. The bore 341 is dimensioned to permit the admittance of a guide pin 36 and suture 60 thereinto, but is insufficient to admit the deformed ring 20 in the collapsed state. Thus in use the ring 20 in the collapsed state is insertable into the sleeve bore 321 from the proximal end 322, and the plunger 348 is also insertable into the sleeve bore 321 from the proximal end 322. Ring discharge from the sleeve bore 321 is achieved by bringing the handle portions 326,346 into apposition, the plunger 348 forcing the ring 20 out of the sleeve's distal end 324.

A series of probes 50 is also provided for measuring the space available in the tunnel 90 for the device 10 of the present invention. Each probe 50 has a measuring distal portion 52 having a rounded distal tip 53 that is inserted into the tunnel 90 after placement of the flexible members 80,82. Successively larger probes 50 are inserted, holding a proximal handle end 54, until a sufficiently snug fit is achieved, which then provides an indication of which size screw 40 to use.

The flexible member affixing method of the present invention is illustrated in FIGS. 6A–F, which present a cross-sectional view along the axis of a bone tunnel 90. The method includes the steps of inserting a pair of flexible members 80,82 into and along the length of a bone tunnel 90 (FIG. 6A) and then measuring the void space remaining in the tunnel 90 (FIG. 6B) with a series of sequentially larger-diameter probes 50.

Next a deformable ring 20 of the correct size corresponding to the bone tunnel 90 diameter is loaded into an inserter 30 as described above. The ring 20 is preloaded with a guide pin 36 extending through the proximal cutout 221, into the proximal end 223, through the bore 206, to the distal end 222, and out the distal cutout 220 (FIG. 6C). The ring 20 also has a repositioning suture 60 looped around the proximal U-shaped section 215 through the bore 206 and tied in a knot to form a loop. The ring 20 is deformed from its free state to the collapsed state and inserted, distal end 222 first, into the proximal end 322 of the inserter sleeve 32.

The suture loop 60 is passed through the plunger bore 341 until it emerges from the plunger's proximal end 342. Then the inserter stylet's plunger 348 is introduced into the sleeve 32, the plunger's distal end 344 inserted into the sleeve's proximal end 322 until the plunger's distal end 344 rests against the ring's proximal end 223. The plunger 348 is used to push the ring 20 through the inserter sleeve's hollow portion 328 to the distal end 324.

Prior to discharging the ring 20 with guide pin 36 and suture 60 into the bone tunnel 90, it is important to ascertain that each flexible member end 80,82 is positioned on an opposite side of the bone tunnel 90 and against the inner surface 92 thereof. The loaded inserter 30 is positioned at the opening of the bone tunnel 90, with the ring 20 oriented so that the flexible member ends 80,82 are positioned between the tunnel's inner wall 92 and the ring's flat sections 212,213. Preferably the width of the ring 20 is commensurate with the diameter of the bone tunnel 92 to ensure an optimal retention of flexible member ends 80,82.

During positioning of the inserter 30, tension is preferably applied to the flexible members' free ends, for example, with a tensiometer. Tension is maintained until the ring expansion is complete.

Once the inserter 30 is properly positioned, the plunger 348 is advanced distalward, pushing the ring 20 out of the sleeve bore 321 and into the bone tunnel 92 (FIG. 6D). In position, a proximal portion 364 of the guide pin 36 preferably remains extending from the tunnel 90, and most of the repositioning suture 60 also extends out of the tunnel 90. A distal portion 362 of the guide pin 36 preferably extends beyond the distal end 222 of the ring 20 through the distal cutout 220.

Once the ring 20 is in the tunnel 90, the cannulated screw 40 of an appropriate diameter, as determined by the probe 50 measurement step, is positioned over the guide pin's proximal portion 364 (FIG. 6E). Next the screw 40 is screwed into the ring's bore 206 from the proximal end 223 with a cannulated screw driver 70 that has a driving portion 72 adapted to engage the screw's driving hole 408, and the ring 20 is progressively expanded with the screw's insertion so as to urge the flat sections 212,213 thereof against the flexible members 80,82, to retain the flexible members in place.

The repositioning suture loop 60 is employed to permit a retrieval of the ring 20 in the event of a misplacement of the ring 20, such as an inadvertent push-through of the ring 20 into a joint space, for example. Once the desired positioning and expansion are achieved (FIG. 6F), the guide pin 36 and retention suture 60 are removed, and the ring/screw 20/40 combination 10 are left in the bone tunnel 90 until healing is achieved. Alternatively, the device 10 can comprise a resorbable material having a time constant of resorption commensurate with or greater than a time of healing.

Figure 6G:
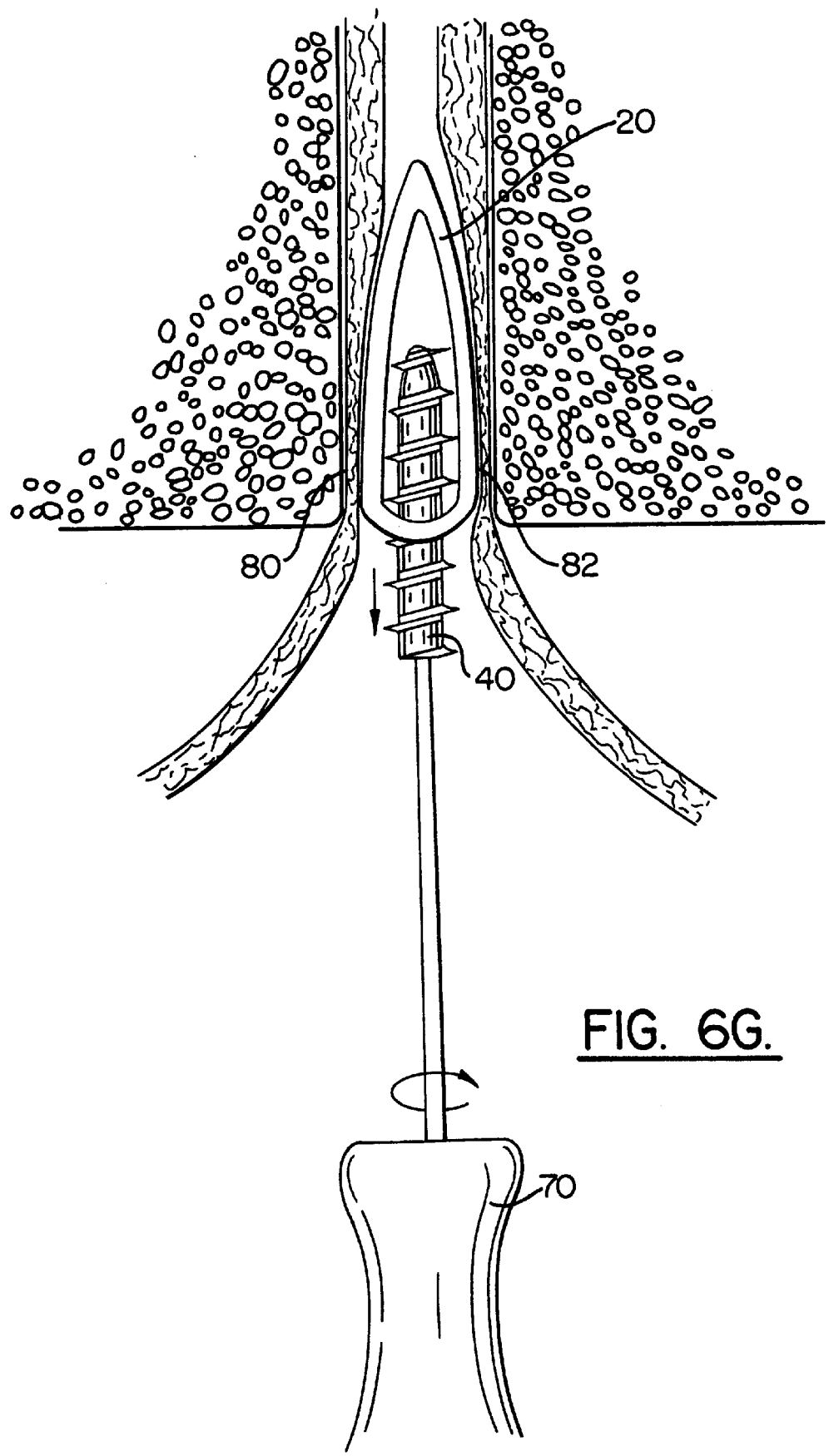

Another feature of the present invention is its ease of removal, which may be desired, for example, in case of failure or intraoperative revision. As illustrated in FIG. 6G, a driver 70 can be used to "unscrew" the screw 40 from the ring 20, and then the ring 20 can be removed.

It may be appreciated by one skilled in the art that additional embodiments may be contemplated, including deformable rings having alternate shapes, but retaining the principle that an outer surface thereof is expanded to urge a flexible member against a bone tunnel wall. Another conceivable embodiment comprises a pair of expandably joined opposed plates, the plates' outer surfaces functionally equivalent to the ring's flat sections 212,213.

Additionally, alternate embodiments of the expanding means may be contemplated, including an insertable bullet-shaped member that can be press fit into the expanding member's bore.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for affixing an end segment of a flexible member within a bone tunnel, the device comprising:

a deformable ring having a first section, a second section in mechanical connection with the first section, a bore extending from a first side to a second side and a proximal cutout at a proximal end, the proximal cutout extending from an outer surface into the bore, the ring dimensioned to slide within a bone tunnel and adapted to permit a positioning of the flexible member end segment between the first section and an inner wall of the bone tunnel, the ring expandable from a collapsed state wherein the first and the second sections are a first distance apart to an expanded state wherein the first and the second sections are a second distance apart greater than the first distance; and means insertable through the proximal cutout into the ring bore for expanding the ring from the collapsed state to the expanded state sufficiently far to urge the ring first section against the flexible member end segment to press and retain the flexible member end segment against the bone tunnel inner wall.

2. The device recited in claim 1, wherein the ring outer surface has means for facilitating a gripping of the flexible member end segment thereagainst.

3. The device recited in claim 2, wherein the gripping facilitating means comprises a plurality of generally transverse grooves therein.

4. The device recited in claim 1, wherein:

the ring has a generally elliptical shape in a cross section normal to the bore in the collapsed state, the first and the second sections comprising two longer, flatter sides of the elliptical shape;

the ring further has two flexible generally U-shaped sections joining the first and the second sections, one each at the proximal end and a distal end of the ring.

5. The device recited in claim 1, wherein the first and the second section each has a width dimensioned for insertion into the bone tunnel.

6. The device recited in claim 1, wherein the expanding means comprises a tapered member adapted to fit within the proximal cutout, a smaller distal end tapering to a larger proximal end, an insertion of the distal end into the ring bore via the proximal cutout thereby causing a progressive expansion of the ring.

7. The device recited in claim 6, wherein the tapered member comprises a screw member having external threads.

8. The device recited in claim 7, wherein the ring comprises a material having a hardness less than a hardness of the screw member; and an insertion of the screw member into the ring bore causes the threads to carve a helical groove in the ring inner surface, the groove assisting to retain the screw member in a desired position.

9. The device recited in claim 7, wherein the screw member has driving means at the proximal end for inserting the screw member into the ring bore.

10. The device recited in claim 9, wherein the driving means comprises a hole shaped to receive an end of a driver.

11. The device recited in Claim I, wherein the ring further has a distal cutout at a distal end extending from the outer surface into the bore, and further comprising a guiding means insertable across the ring bore from the proximal cutout to the distal cutout prior to an insertion of the expanding means, the expanding means slidable along the guiding means during insertion, for facilitating the expanding means insertion into the ring bore.

12. The device recited in claim 11, wherein the ring further has a pair of opposed longitudinal grooves, one groove in an inner surface of each of the first and the second sections, extending from the distal cutout to the proximal cutout, and wherein the guiding means comprises an elongated member dimensioned to reside within the opposed grooves when the ring is in the collapsed state.

13. The device recited in claim 12, wherein the guiding means comprises a guide pin, and wherein the expanding means comprises a cannulated screw having a longitudinally extending bore therethrough dimensioned to slidably admit the guiding means thereinto.

14. The device recited in claim 1, further comprising device repositioning means detachably affixed to the ring and adapted to extend outside the bone tunnel when the ring and expanding means are therewithin, for assisting in repositioning the ring and expanding means if desired.

15. The device recited in claim 14, wherein the repositioning means comprises an elongated element looped around the proximal end of the ring and through the bore.

16. The device recited in claim 15, wherein the elongated element comprises a loop of suture material.

17. A device for affixing an end segment of a flexible member within a bone tunnel, the device comprising:

an expandable member having a first section, a second section in mechanical connection with the first section, a space therebetween, and an opening extending from outside the expandable member into the space, the expandable member dimensioned to slide within a bone tunnel and adapted to permit a positioning of the flexible member end segment between the first section and an inner wall of the bone tunnel, the expandable member expandable from a collapsed state wherein the first and the second sections are a first distance apart to an expanded state wherein the first and the second sections are a second distance apart greater than the first distance; and means insertable through the opening into the space for expanding the expandable member from the collapsed state to the expanded state sufficiently far to urge the expandable member first section against the flexible member end segment to press and retain the flexible member end segment against the bone tunnel inner wall, the expanding means comprising a member adapted to fit within the opening, the member tapered along at least a portion thereof between a distal end and a proximal end, an insertion of the member from the distal end into the space via the opening thereby causing a progressive expansion of the expandable member.

18. The device recited in claim 17, wherein the expanding means comprises a tapered member adapted to fit within the proximal opening, a smaller distal end tapering to a larger proximal end, an insertion of the distal end into the space via the proximal opening thereby causing a progressive expansion of the ring.

19. The device recited in claim 18, wherein the opening comprises a proximal opening positioned generally at a proximal end and the expandable member further has a distal opening at a distal end extending from outside the expandable member into the space, and further comprising a guiding means insertable across the space from the proximal opening to the distal opening prior to an insertion of the expanding means, the expanding means slidable along the guiding means during insertion, for facilitating the expanding means insertion into the space.

20. A system for affixing an end segment of a flexible member within a bone tunnel, the system comprising:

an expandable member having a first section, a second section in mechanical connection with the first section, a space therebetween, and an opening extending from outside the expandable member into the space, the expandable member dimensioned to slide within a bone tunnel and adapted to permit a positioning of the flexible member end segment between the first section and an inner wall of the bone tunnel, the expandable member expandable from a collapsed state wherein the first and the second sections are a first distance apart to an expanded state wherein the first and the second sections are a second distance apart greater than the first distance;

means insertable through the proximal opening into the space for expanding the expandable member from the collapsed state to the expanded state sufficiently far to urge the expandable member first section against the flexible member end segment to press and retain the flexible member end segment against the bone tunnel inner wall;

means for guiding the expanding means into the space, the guiding means releasably engageable with the expandable member and with the expanding means; and insertion means having means for supporting the expandable member for insertion into the bone tunnel.

21. The system recited in claim 20, wherein the insertion means comprises:

a sleeve having a bore dimensioned to admit the expandable member therewithin; and means for ejecting the expandable member from the bore into the bone tunnel.

22. The system recited in claim 21, wherein the ejecting means comprises a plunger means slidable within the sleeve bore proximal of the expandable member and dimensioned sufficiently long to eject the expandable member completely from the bore.

23. The system recited in claim 22, a guide pin insertable across the space from the opening to a distal end prior to an insertion of the expanding means, the expanding means comprising a cannulated screw having a longitudinally extending bore therethrough dimensioned to slidably admit the guide pin thereinto, the screw slidable along the guide pin, for facilitating screw insertion into the space.

24. The system recited in claim 20, further comprising a probe means having means for measuring a diameter of a remaining void space in the bone tunnel following an insertion of the flexible member end segment, the measured void space determining a size of the expanding means to be utilized.

25. The system recited in claim 24, wherein the probe means comprises a plurality of probes of varying diameters, for permitting a probing of the void space with successively larger probes.

26. A method for attaching a flexible member end segment within a bone tunnel, the method comprising the steps of:

positioning a flexible member end segment in a bone tunnel;

inserting a deformable ring into the bone tunnel, the flexible member end segment positioned between an inner wall of the bone tunnel and an outer surface of the ring; and deforming the ring so as to urge the outer surface thereof against the flexible member end segment for retaining the flexible member end segment in place within the bone tunnel.

27. The method recited in claim 26, wherein the ring deforming step comprises inserting a tapered member into a bore of the ring, a smaller end first, so that a progressive insertion thereof causes an expansion of the ring.

28. The method recited in claim 27, wherein the ring has a generally elliptical shape in a cross section normal to the bore and a generally flat section, the positioning step comprising positioning the flexible member end segment between the bone tunnel inner wall and the flat section of the ring.

29. The method recited in claim 26, wherein:

the flexible member inserting step comprises inserting a pair of flexible members;

the ring inserting step comprises inserting the ring with a first flexible member end segment between a first section of the ring and the bone tunnel inner surface and with a second flexible member end segment between a second section of the ring generally opposed to the first section and the bone tunnel inner surface; and the ring deforming step comprises expanding a distance between the first and the second sections from a collapsed state to an expanded state.

30. A method for attaching a flexible member end segment within a bone tunnel, the method comprising the steps of:

positioning a flexible member end segment in a bone tunnel;

inserting an expandable member into the bone tunnel, the flexible member end segment positioned between an inner wall of the bone tunnel and an outer surface of the expandable member;

expanding the expandable member so as to urge the outer surface thereof against the flexible member end segment for retaining the flexible member end segment in place within the bone tunnel, the expanding step comprising introducing a tapered member into a space within the expandable member to cause a progressive expansion thereof.

31. The method recited in claim 30, further comprising the steps of:

measuring a void space remaining within the bone tunnel following the positioning step; and selecting a tapered member having a size based upon the measured the void space.

32. The method recited in claim 31, further comprising the step of guiding the tapered member during the introducing step with the use of a guide means situated within the expandable member.

33. The method recited in claim 30, further comprising the step, following the expanding step, of removing the expandable member from the bone tunnel.

34. A method for attaching a flexible member end segment within a bone tunnel, the method comprising the steps of:

positioning a pair of flexible member end segments in a bone tunnel, the segments generally opposed against an inner wall of the bone tunnel;

measuring a void space remaining within the bone tunnel;

loading an inserter with a deformable ring having a guide wire positioned across a bore thereof;

inserting the deformable ring and guide wire into the bone tunnel, the flexible member end segments positioned between the inner wall of the bone tunnel and outer surfaces of two generally opposed sections of the ring;

inserting a narrower end of a tapered screw between the ring opposed sections;

advancing the screw between the ring opposed sections, thereby expanding a distance between the ring opposed sections, urging the outer surfaces thereof against the flexible member end segments, and retaining the flexible member end segments in place within the bone tunnel.

35. The method recited in claim 34, further comprising the step of exerting tension on the flexible member end segments prior to the deformable ring and guide wire insertion step.

\* \* \* \* \*